United States Patent [19]
Marhold et al.

[11] Patent Number: 6,075,160
[45] Date of Patent: Jun. 13, 2000

[54] 4-CYANO-2,5-DIFLUOROANILINE PREPARATION PROCESS

[75] Inventors: Albrecht Marhold, Leverkusen; Dietmar Bielefeldt, Ratingen; Bernd Gallenkamp, Wuppertal, all of Germany

[73] Assignee: Bayer Aktiengesellschaft, Leverkusen, Germany

[21] Appl. No.: 09/011,943

[22] PCT Filed: Aug. 19, 1996

[86] PCT No.: PCT/EP96/03642

§ 371 Date: Feb. 20, 1998

§ 102(e) Date: Feb. 20, 1998

[87] PCT Pub. No.: WO97/08136

PCT Pub. Date: Mar. 6, 1997

[30] Foreign Application Priority Data

Aug. 30, 1995 [DE] Germany ............ 195 31 895

[51] Int. Cl.$^7$ .................................................. C07C 255/00
[52] U.S. Cl. ........................................................ 558/418
[58] Field of Search .............................. 558/418

[56] References Cited

U.S. PATENT DOCUMENTS 4,504,660  3/1985  Klaubert et al. .................. 558/418

FOREIGN PATENT DOCUMENTS 0 224 001  6/1987  European Pat. Off. .
0 415 595  3/1991  European Pat. Off. .
0 497 213  8/1992  European Pat. Off. .

OTHER PUBLICATIONS

Ohmori et al., Journal of Medicinal Chemistry, vol. 37, No. 4 (1994) pp. 467–475.

*Primary Examiner*—Robert W. Ramsuer
*Assistant Examiner*—Joseph Murray
*Attorney, Agent, or Firm*—Sprung Kramer Schaefer & Briscoe

[57] ABSTRACT

The present invention relates to a process for preparing 4-cyano-2,5-difluoroaniline, which is an intermediate in the preparation of herbicides or liquid crystals.

3 Claims, No Drawings

4-CYANO-2,5-DIFLUOROANILINE PREPARATION PROCESS

This application is a 371 of PCT/EP96/03642 Aug. 19, 1996.

The invention relates to a process for preparing 4-cyano-2,5-difluoroaniline, which is an intermediate in the preparation of herbicides or liquid crystals.

The known two-step process for preparing 4-cyano-2,5-difluoroaniline starts from 2,5-difluoroaniline (see EP-A1 0 224 001). In the first stage this is brominated to give 4-bromo-2,5-difluoroaniline. In the second stage, the bromine is replaced by cyano. In addition to an at least equimolar quantity of copper cyanide for the reaction, it also requires an approximately 5-fold molar quantity of 10% sodium cyanide solution for work-up. Significant disadvantages include the cost of copper cyanide and the processing of waste water, which is problematical not merely because of the copper which is bound as cyano complex, the lengthy extractive work-up, in particular the large amount of dichloromethane required, and the handling of large quantities of very poisonous sodium cyanide solution.

It has been found that 4-cyano-2,5-difluoroaniline is obtained in high yield and purity if 2,4,5-trifluorobenzonitrile is reacted with an excess of ammonia at elevated temperatures, optionally in the presence of a diluent.

Surprisingly, even a large excess of ammonia does not lead to a di- or triamine. Furthermore, it is very surprising that exchange only takes place selectively in the 4-position and not in the 2-position. Analogous reactions using 2,4-difluorobenzonitrile under the conditions according to the invention give the two possible amines in an approximate ratio of 1:1.

The 2,4,5-trifluorobenzonitrile which is required as starting material is commercially available and can be prepared, for example, from 2,4-dichloro-5-fluorobenzoyl chloride by fluorination, amidation and subsequent dehydration.

Suitable diluents for carrying out the reaction according to the invention are water, certain organic solvents and any mixtures thereof. Those which may be mentioned by way of example are: aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene or dichlorobenzene; ethers, such as diethyl ether, diisopropyl ether, methyl tert-butyl ether, methyl tert-amyl ether, dioxane, tetrahydrofuran, 2-methyltetrahydrofuran, 1,2-dimethoxyethane, diethylene glycol dimethyl ether, 1,2-diethoxyethane or anisole. In principle, the use of a diluent is preferred. Preferred solvents are dioxane, tetrahydrofuran, toluene and water.

The reaction is carried out at temperatures of from 50 to 150° C., preferably from 80 to 130° C.

The reaction is generally carried out at increased pressure. It is preferably carried out at pressures which correspond to at least the autogenous pressure of the reaction mixture at the reaction temperature. A pressure of from 2 to 50 bar gauge is particularly preferred.

In general, the reaction according to the invention is carried out using from 1.5 to 50 mol, preferably from 2 to 20 mol, of ammonia and, if desired, from 0.1 to 3 l, preferably from 0.3 to 2 l, of diluent per mole of 2,4,5-trifluorobenzonitrile.

In a preferred embodiment of the reaction step of the process according to the invention, the nitrile, with the diluent, is introduced into a sealed reaction vessel and heated to the reaction temperature. Liquid ammonia is then pumped in against the container pressure at such a rate that the internal temperature can be kept constant.

In a preferred embodiment of the work-up step of the process according to the invention, after the reaction is complete the system is cooled, the container is decompressed and the excess ammonia and the diluent are removed, if necessary under reduced pressure. To isolate the 4-cyano-2,5-difluoroaniline, the residue is stirred with water, and the crystals are separated off, slurried with water, separated off again and finally dried.

The 4-cyano-2,5-difluoroaniline which can be prepared by the process of the invention can be used, for example, as an intermediate in the preparation of herbicides or liquid crystals (see, for example, EP-A1 648 772; DE-OS 38 351 68; JP 02 243 676).

EXAMPLE 1

515 g of 2,4,5-trifluorobenzonitrile in 2000 ml of tetrahydrofuran are introduced into an autoclave and heated to 100° C. 250 ml of liquid ammonia are then pumped in at such a rate that the temperature remains in the range from 100 to 105° C. The mixture is then stirred at this temperature for 8 h and then cooled. The pressure reaches a maximum of 22 bar gauge. After the ammonia has been blown off, the solvent is removed using a rotary evaporator. The residue is stirred into 500 ml of water and placed on a suction filter. After filtering with suction, the residue is again slurried with 200 ml of water and filtered with suction. Drying in a vacuum at 40° C. gives 482 g (95.4% of theory) of 4-cyano-2,5-difluoroaniline having a melting point of from 99 to 100° C.

EXAMPLE 2

4500 ml of liquid ammonia are added at approximately 20° C. to a solution of 3000 g of 2,3,5-trifluorobenzonitrile in 10 l of methyl tert-butyl ether in a 40 l stainless-steel autoclave fitted with an anchor stirrer. In addition to the autogenous pressure of the reaction mixture, 10 bar of nitrogen is injected, and the mixture is reacted at 100° C. for 16 hours. After the unreacted ammonia has been removed and the solvent has been extracted with water, the solvent is distilled off at from 40 to 60° C. (200 to 300 mbar). The residue obtained is 2839 g of pure product, corresponding to a yield of 96.5% of theory.

We claim:

1. Process for preparing 4-cyano-2,5-difluoroaniline, wherein 2,4,5-trifluorobenzonitrile is reacted with an excess of ammonia optionally in the presence of a diluent, wherein the reaction is carried out at temperatures of from 50 to 150° C. and wherein the reaction is carried out at increased pressure.

2. Process for preparing 4-cyano-2,5-difluoroaniline according to claim 1, wherein the reaction uses from 1.5 to 50 mol of ammonia and, if desired, from 0.1 to 3.1 of diluent per mole of 2,4,5-trifluorobenzonitrile.

3. Process for preparing 4-cyano-2,5-difluoroaniline according to claim 1, wherein the nitrile, with the diluent, is introduced into a sealed reaction vessel and heated to the reaction temperature, the liquid ammonia is pumped in against the container pressure at such a rate that the internal temperature is maintained, then after the reaction is complete the system is cooled, the excess ammonia and the diluent are removed, if necessary under reduced pressure, the residue is stirred with water, and the crystals are separated off, washed with water or slurried in water, separated off again and finally dried.

* * * * *